United States Patent
Morazzoni et al.

(10) Patent No.: US 7,429,673 B2
(45) Date of Patent: Sep. 30, 2008

(54) TRPV1 AGONISTS, FORMULATIONS CONTAINING THEM AND USES THEREOF

(75) Inventors: Paolo Morazzoni, Milan (IT); Antonella Riva, Milan (IT); Gabriele Fontana, Milan (IT); Giovanni Appendino, Novara (IT); Vincenzo Di Marzo, Pozzuoli (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 11/658,737

(22) PCT Filed: Jul. 6, 2005

(86) PCT No.: PCT/EP2005/007292
§ 371 (c)(1), (2), (4) Date: Apr. 6, 2007

(87) PCT Pub. No.: WO2006/010445
PCT Pub. Date: Feb. 2, 2006

(65) Prior Publication Data
US 2008/0132573 A1 Jun. 5, 2008

(30) Foreign Application Priority Data
Jul. 30, 2004 (IT) .......................... MI2004A1566

(51) Int. Cl.
C07C 69/76 (2006.01)
A61K 31/195 (2006.01)
(52) U.S. Cl. ..................... 560/103; 560/106; 560/110; 514/561; 514/563
(58) Field of Classification Search ................ 560/103, 560/106, 110; 514/561, 563
See application file for complete search history.

(56) References Cited
FOREIGN PATENT DOCUMENTS

EP 0 132 113 1/1985
EP 1 426 047 6/2004
WO WO 00/16756 3/2000

OTHER PUBLICATIONS

Appendino, Giovanni et al: "N-Acylvanillamides: Development of an Expeditious Synthesis and Discovery of New Acyl Templates for Powerful Activation of the Vanilloid Receptor" Journal of Medicinal Chemistry, 45(17), 3739-3745 CODEN: JMCMAR; ISSN: 0022-2623, 2002, XP002346966 cited in the application p. 3742; compound 1Q, p. 3742, col. 1, last paragraph—p. 3742, col. 2, paragraph 1.

Janusz J M et al: "Vanilloids. 1. Analogs of Capsaicin With Antinociceptive and Antiinflammatory Activity" Journal of Medicinal Chemistry, American Chemical Society. Washington, US, vol. 36, No. 18, 1993, pp. 2595-2604, XP001008868 ISSN: 0022-2623 table III; compound 36.

Appendino, Giovanni et al: "Development of the first ultra-potent "capsaicinoid" agonist at transient receptor potential vanilloid type 1 (TRPV1) channels and its therapeutic potential" Journal of Pharmacology and Experimental Therapeutics, 312(2), 561-570 CODEN: JPETAB; ISSN: 0022-3565, 2005, XP008053161, p. 566, col. 1, line 30-line 35 p. 566; table 1.

*Primary Examiner*—Sikarl A Witherspoon
(74) *Attorney, Agent, or Firm*—Young & Thompson

(57) ABSTRACT

The compounds of the general formula (I) in which X is represents two hydrogen atoms, a π-bond, oxygen or methylene: R2 is a $C_6$-$C_{12}$ aryl, or arylalkyl residue: R3 is hydrogen, 2-hydroxyethyl or 2-aminoethyl are useful for the treatment of pathologies mediated by vanilloid receptors type I.

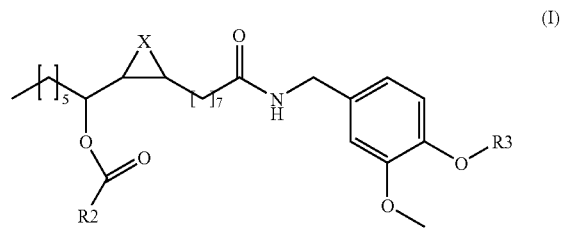

6 Claims, No Drawings

TRPV1 AGONISTS, FORMULATIONS CONTAINING THEM AND USES THEREOF

The present invention relates to ricinoleic acid derivatives with agonistic activity towards the vanilloid receptor type-1.

BACKGROUND OF THE INVENTION

The vanilloid receptor type 1 (VR1 or TRPV1) belongs to the wide family of transient receptor potential cationic channels (TRPV) with six trans-membrane domains. TRPV1 is the only TRPV channel that is presently known to be activated by some natural products, capsaicin and resiniferatoxin being the most known and studied (Sterner and Szallasi, *Trends Pharmacol. Sci.* 1999, 20, 459-465). Its is to date recognized that, while other TRPV channels, such as TRPV2, TRPV3 and TRPV4 (also known as "VR1-like (VRL) receptors"), are solely responsive to mechanical, osmotic or thermal stimuli and are in principle evenly distributed in the various tissues of mammals, TRPV1 specifically acts as a molecular integrator of pain stimulation induced, for instance, by heat, protons and vegetable toxins and is mainly expressed in peripheral sensory type C and Aδ fibres (Gunthorpe et al., *Trends Pharmacol. Sci.* 2002, 23, 183-191).

VR1-Knockout studies on transgenic mice univocally proved the role of TRPV1 in partial perception and transmission of "thermal" or "inflammatory" pain (Caterina et al., *Science* 2000, 288, 306-313; Davis et al., *Nature* 2000, 405, 183-187). Other studies suggested that TRPV1 is involved also in intestinal inflammatory disorders (Yiangou et al., *Lancet* 2001, 357, 1338-1339), neuropatic pain (Walker et al., *J. Pharmacol. Exp. Ther.* 2003, 304, 56-62), fecal incontinence and pathological cough (Chung and Chang, *Pulm. Pharmacol. Ther.* 2002, 15, 335-338). TRPV1 apparently plays a fundamental role also in the control of urinary bladder function (Birder et al., *Nat. Neurosci.* 2002, 5, 856-860) and in the control of neuronal plasticity, body temperature, food intake, energy expenditure, and movement (Di Marzo et al., *Eur. J. Pharmacol.* 2001, 420, 123-131).

Neurons expressing TPRV1 receptors can be desensitised immediately after activation by some agonists, such as capsaicin. From the practical point of view, the starting burning sensation due to the agonist action is overcome by a paradox effect. VR1 tachyphylaxis can also account for other medicinal effects described for capsaicin and chili pepper, such as the well-known anti-emetic and anti-inflammatory effects and the neuroprotective effect against glutamate excitotoxicity. Capsaicin and its analogue resiniferotoxin are also used in the treatment of urinary incontinence (wherein nerve ends characterized by the presence of VR participate in the transmission of the bladder emptying reflex), whereas capsaicin synthetic derivatives, the most known being olvanil, have been patented as oral analgesics. The pharmaceutical industry is, however, still remarkably interested in the development of more potent TRPV1 agonists.

DISCLOSURE OF THE INVENTION

The compounds of the invention have the following general formula (I)

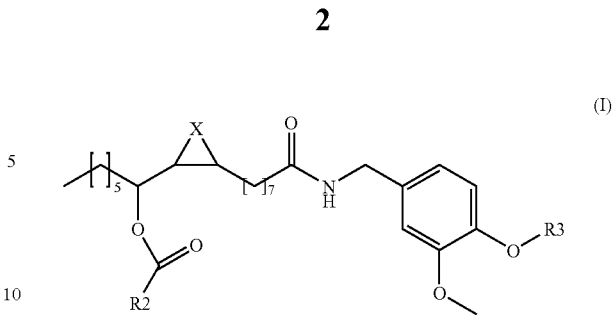

in which
X represents two hydrogen atoms, a π-bond, oxygen or methylene;
R2 is a $C_6$-$C_{12}$ aryl or arylalkyl residue;
R3 is hydrogen, 2-hydroxyethyl or 2-aminoethyl.
R2 is preferably phenyl, benzyl or phenethyl and R3 is preferably hydrogen.

These compounds are potent TPVR1 agonists and are therefore useful for the treatment of pain or urinary incontinence or intestinal inflammatory disorders.

The present invention also relates to pharmaceutical compositions comprising the compounds of formula (I) as active principles in effective amount.

The compounds of the invention can be in racemic or enantiomerically pure form, more preferably 12R. The configuration of the double bond can be E or Z, more preferably Z. The present invention also includes pharmacologically acceptable salts of the compounds of formula (I).

The compounds of the invention can be synthesised for example through the methods reported hereinbelow; other reagents and starting materials can be chosen in order to obtain other compounds of formula (I).

According to the simplest synthetic approach, the compounds of the invention are prepared from ricinoleic acid vanillamide, according to Scheme 1.

Scheme 1

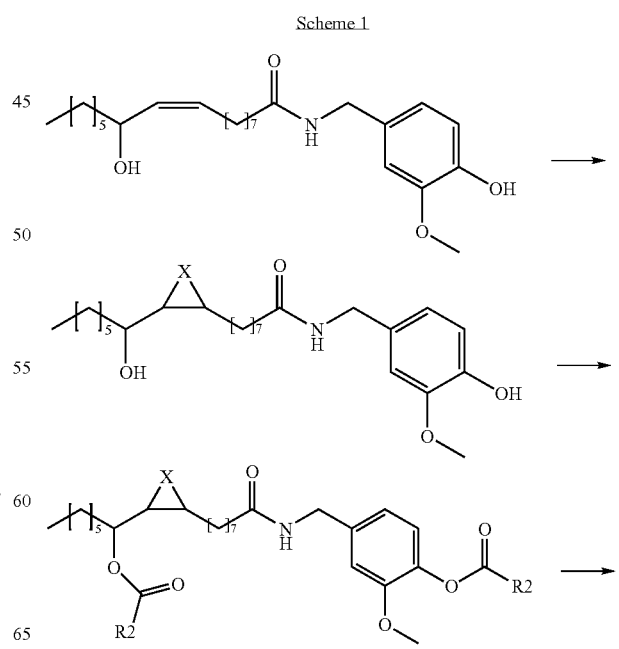

-continued

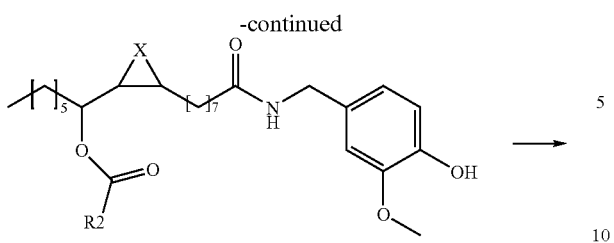

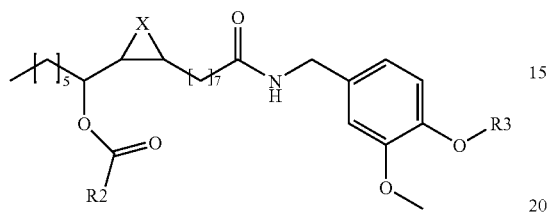

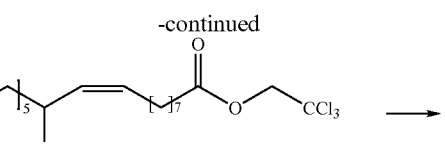

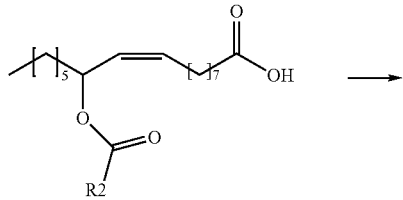

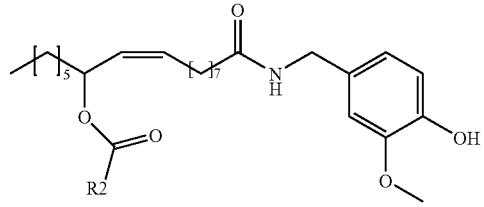

Ricinoleic acid vanillamide, prepared according to the literature, is optionally subjected to cyclopropanation or epoxidation and the resulting intermediate is esterified with an appropriate acylating agent. Activated carboxylic acids derivatives suitable for the esterification are acid halides, especially chlorides, as well as mixed anhydrides or adducts with carbodiimide, according to the methods known in the art. The ester of the para-hydroxyl of the vanillamine residue is subsequently selectively hydrolysed to give the corresponding hydroxy derivative, which is an object of the present invention. If desired, the phenolic hydroxyl can be subsequently etherified with an aminoethyl or a hydroxyethyl residue.

Alternatively, the intermediates useful for the synthesis of the compounds of the present invention can be obtained also starting from trichloroethanol ricinoleate according to Scheme 2.

Scheme 2

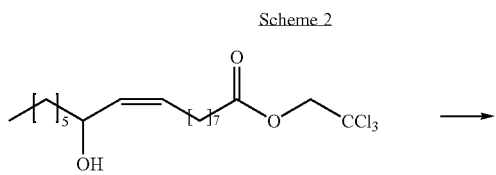

Trichloroethanol ricinoleate, prepared according to the literature, is acylated at the 12 position with an activated carboxylic acid, similarly to what reported above. The trichloroethyl ester is then selectively hydrolysed to give 12-acylricinoleic acid which is subsequently converted to amide by condensation with vanillamine.

The same methods can be successfully applied to the trans and 12-S isomers, or to the saturated analogous of natural ricinoleic acid.

The biological activity of the products of the invention was measured both in vitro and in vivo.

The in vitro effect of the compounds of formula (I) on TRPV1 was studied by measuring the concentration of intracellular calcium in HEK-293 cells (which overexpress human TRPV1); calcium concentration in the presence of 4 μM ionomycin was taken as the maximum reference value (Hayes et al., *Pain* 2000, 88, 205-215). The results are reported in the following table 1.

TABLE 1

| Structure | $pEC_{50}$ DMSO | $pEC_{50}$ methanol |
|---|---|---|
| Capsaicin | | |
| Compound of example 15 | 8.27 ± 0.15 | 8.39 ± 0.18 |
| Acetyl rinvanil | | |
| Compound of example 2 and example 6 | 9.99 ± 0.14 | 10.18 ± 0.17 |
| Compound of example 9 | 9.89 ± 0.16 | 9.54 ± 0.11 |
| Compound of example 12 | 9.92 ± 0.14 | 9.80 ± 0.10 | pEC50 values for TPVR1 in DMSO and methanol

TABLE 1-continued pEC50 values for TPVR1 in DMSO and methanol

| Structure | pEC$_{50}$ DMSO | pEC$_{50}$ methanol |
|---|---|---|
| Compound prepared according to Appendino et al., J. Med. Chem. 2002, 45, 3739-3745 | 9.30 ± 0.19 | 9.40 ± 0.18 |

The activity of the compound of example 2 was also evaluated in rats through the in vivo test of induced urinary incontinence.

Sprague Dawley rats (250±10 g) were anaesthetized with chloral hydrate. The urinary bladder was opened through an incision along the abdomen median line, and the adipose tissue surrounding the urethra and ureters was removed. The proximal urethra was then tied up with non-absorbable surgery thread to create partial urethral obstruction. After 8 weeks, alteration of bladder functionality was observed and the cystometric pattern was altered, the number of minctions per hour being particularly increased.

On the treatment day, the compound of example 2, the compound prepared according to Appendino et al. and resiniferotoxin as the reference standard were solubilised in ethanol and instilled in the bladder at the concentration of 50 nM. The instillation lasted 30 min: during this period the infusion pump for the saline was turned off. After incubation, the bladder was emptied of any medicament solution, then the infusion pump was turned on again.

A significant increase in the number of minctions per hour was observed in non treated operated animals. On the contrary, in animals treated with the compound of the invention and with resiniferotoxin the number of minctions remained similar to that of non-operated animals. Very low activity was also observed also for the product of Appendino et al.

The results of the experiment are reported in the following table 2.

TABLE 2

| Treatment | N° of minctions per hour |
|---|---|
| Healthy rats (ethanol) | 18 ± 2 |
| Operated rats (ethanol) | 30 ± 2 |
| Compound of example 2 | 19 ± 2 |
| Compound according to Appendino et al. | 25 ± 3 |
| Resiniferotoxin | 17 ± 2 |

As potent agonists of the TPRV1 receptor, compounds (I) can be used in the treatment of urinary incontinence, in the relief of neuropatic pain and in the therapy of inflammatory intestinal disorders.

The invention also relates to pharmaceutical compositions comprising compounds (I) in combination with suitable carriers or diluents. The pharmaceutical compositions of the invention can be administered through different administration routes, for example through the oral, rectal, intravenous, intramuscular, subcutaneous, intrathecal, epidural or intracerebroventricular route. Suitable carriers for injectable formulations comprise oils, propylene or ethylene glycol, physiological solution, ethanol, vegetable oils and isopropyl myristate or other solvents commonly used for the preparation injectable solutions.

To prepare injectable formulations the compounds of the invention can be dissolved, suspended or emulsified in aqueous solvents, such as physiological solution, 5% dextrose, or non-aqueous solvents such as vegetable oil, saturated synthetic glycerides, esters of long-chain aliphatic acids or propylene glycol. The formulations can also include conventional excipients, such as solubilizing agents, isotonic agents, suspending agents, emulsifiers, stabilizing agents and preservatives.

For the topical use, the compounds of the invention can be formulated as creams or ointments.

The pharmaceutical composition of the invention can be used:
- to alleviate pain caused by post-herpetic neuralgia, diabetic neuropathy, post-mastectomy syndrome, sympathetic reflex dystrophy, trigeminal neuralgia, oral neuropathic pain, osteoarthritis, rheumatoid arthritis, fibromialgia, Guillain-Barrè syndrome;
- to alleviate non-treatable pain caused by bilateral peripheral neuropatia;
- to alleviate itching caused by psoriasis, hemodialysis, aquagenic itching, vulvar vestibulitis, notalgia paresthetica, brachioradial itching;
- to treat cluster headaches, rhinitis vasomotoria or allergic rhinitis (as intranasal drops);
- to treat bladder hypersensibility or spinal detrusor hyperreflexia (as intrabladder solution).

The compounds of the present invention have potent analgesic effect and potential antiinflammatory activity, and the pharmaceutical formulations containing them can be used to alleviate or treat acute or chronic inflammatory pain, inflammation and urgency incontinence.

The compounds of the invention can be used in the form of pharmacologically acceptable salts, alone or in appropriate combination, optionally in admixture with other active ingredients.

The dose of the compounds of the invention varies depending on the conditions and weight of the patient, severity of the disease, pharmaceutical form, administration route and duration, and can be established by the expert clinician. In principle, the dose will range from 0.1 µg to 100 mg/kg, preferably from 1 µg to 100 mg/kg/die. The preparation can be administered as single or repeated dose. The compounds percentages in the compositions can range from 0.0001 to 10% by weight, preferably from 0.0001 to 1% on the composition weight.

The following examples illustrate the invention in greater detail.

EXAMPLE I 12,4'-Diphenylacetyl Rinvanil

A solution of 1.56 g of rinvanil (3.6 mmol) in toluene (20 ml) is added with 2 eqmol of phenylacetic acid (1.0 g, 7.2 mmol), 2 eqmol of dicyclohexylcarbodiimide (1.45 g, 7.2 mmol) and 1 eqmol of DMAP (440 mg, 3.6 mmol). The reaction is left under stirring at room temperature and monitored by TLC (6:4 petroleum ether/ethyl acetate Rfp=0.31; Rfa=0.60). After 3 hours the mixture is filtered and the solvent is evaporated off. The resulting crude can either be used as such for the subsequent step or recovered by column chromatography.

$^1$H-NMR (300 MHz, CDCl$_3$): δ 7.39-7.17 (m, 10H), 6.93 (d, J=7.9 Hz, 1H), 6.85 (d, J=2.0 Hz, 1H), 6.80 (dd, J=7.9, 2.0 Hz, 1H), 5.86 (br s, 1H), 5.44 (m, 1H), 5.29 (m, 1H), 4.87 (quint, J=6.0 Hz, 1H), 4.38 (d, J=5.8 Hz, 2H), 3.88 (s, 2H), 3.74 (s, 3H), 3.58 (s, 2H), 2.29 (t, J=7.4 Hz, 2H), 2.20 (t, J=7.4 Hz), 2.01 (m, 2H), 1.66 (m, 2H), 1.52 (m, 2H), 1.29 (br m), 1.21 (br m), 0.86 (br t, J=7.1 Hz, 3H).

$^{13}$C-NMR (75 MHz, CDCl$_3$): 175.5 (s), 173.9 (s), 149.3 (s), 147.6 (s), 134.4 (s), 132.1 (d), 130.4 (s), 128.3 (d), 128.6 (d), 127.1 (d), 124.2 (d), 120.8 (d), 114.4 (d), 110.8 (d), 74.8 (d), 56.0 (q), 43.5 (t), 41.8 (t), 36.9 (t), 33.5 (t), 31.8 (t), 29.5 (t), 29.3 (t), 28.18 (t), 27.4 (t), 25.8 (t), 25.2 (t), 22.6 (t), 14.2 (q).

CI-MS: 670 (M+H)$^+$.

EXAMPLE II

12-Phenylacetyl Rinvanil

The crude 12,4'-diphenylacetyl rinvanil (3.6 mmol, calculated) of example I is dissolved in dichloromethane (20 ml) and treated with 5 eqmol of pyrrolidine (1.52 ml, 1.30 g, 18.0 mmol). The reaction is magnetically stirred at room temperature and monitored by TLC (6:4 petroleum ether/ethyl acetate Rfp=0.8; Rfa=0.5). After 3 hours the reaction is worked up by washing with 2N H$_2$SO$_4$ and brine. The organic phase is dried (Na$_2$SO$_4$), filtered and evaporated and the residue is purified by column chromatography (37 g of silica gel, packed with 7:3 petroleum ether/ethyl acetate and eluted with 6:4, 4:6; fractions of about 20 ml are collected). 1.6 g (80%) of phenylacetyl rinvanil is obtained. The compound is an oil at room temperature, but in the freezer solidifies to a white powder.

$^1$H NMR (300 MHz, CDCl$_3$): δ 7.26 (m, 5H), 6.85 (d, S=7.9 Hz, 1H), 6.80 (d, J=2.0 Hz, 1H), 6.74 (dd, J=7.9, 2.0 Hz, 1H), 5.69 (br s, 1H), 5.65 (br s, 1H), 5.41 (m, 1H), 5.27 (m, 1H), 4.85 (quint, J=6.0 Hz, 1H), 4.34 (d, J=5.8 Hz, 2H), 3.86 (s, 3H), 3.57 (s, 2H), 2.25 (m, 2H), 2.17 (t, J=7.4 Hz), 1.95 (m, 2H), 1.63 (m, 2H), 1.50 (m, 2H), 1.27 (br m), 1.20 (br m), 0.85 (br t, J=7.1 Hz, 3H).

$^{13}$C-NMR (75 MHz, CDCl$_3$): 177.0 (s), 173.5 (s), 171.7 (s), 156.6 (s), 147.2 (s), 145.4 (s), 141.6 (d), 136.8 (s), 132.7 (S), 130.2 (d), 129.5 (d), 129.3 (d), 128.5 (d), 128.3 (d), 127.5 (d), 127.0 (d), 126.2 (d), 124.1 (d), 120.6 (d), 114.9 (d), 110.9 (d), 106.1 (d), 74.6 (d), 56.3 (q), 43.8 (t), 43.4 (t), 41.9 (t), 36.6 (t) 4, 31.8 (t), 29.1 (t), 27.2 (t), 25.9 (t), 25.3 (t), 22.6 (t), 13.9 (q).

CI-MS: 552 (M+H)$^+$.

EXAMPLE III

2',2',2'-Trichloroethyl Ricinoleate 3 g of ricinoleic acid (M.W.=298.47; 10.07 mmol) are dissolved in 30 ml of toluene, added with 2 eqmol of trichloroethanol (M.W.=149.40; 20.14 mmol; 3.0 g; d=1.55; 1.9 ml), 1 eqmol of dicyclohexylcarbodiimide (M.W.=202; 10.07 mmol; 2.0 g) and 1 eqmol of DMAP (M.W.=122; 10.07 mmol; 1.23 g). The resulting mixture is magnetically stirred at room temperature and the reaction is monitored by TLC (8:2 hexane/hetyl acetate Rfp=0.14; Rfa=0.53). After 18 hours the mixture is filtered and the solvent is evaporated off. The crude is purified by filtration on silica gel, using 9:1 petroleum ether/ethyl acetate as the eluent. 4.3 g of product (quantitative yield) are obtained.

$^1$H NMR (300 MHz): δ 5.53 (m, 1H), 5.41 (m, 1H), 4.73 (s, 2H), 3.60 (br t, J=6.0 Hz, 1H), 2.44 (t, J=7.4 Hz, 2H), 2.20 (t, J=6,3 Hz, 2H), 2.03 (m, 2H), about 1.68 (m, 2H), about 1.20 (br m, 20H), 0.87 (br t, J=7.1 Hz, 3H).

EXAMPLE IV

2',2',2'-Trichloroethyl 12-Phenylacetyl Ricinoleate 4.3 g of 2',2',2'-trichloroethyl ricinoleate (10.7 mmol) are dissolved in 30 ml of toluene and added with 2.5 eqmol of phenylacetic acid (3.4 g, 25.2 mmol), 2.5 eqmol of dicyclohexyl carbodiimide (5.0 g, 25.2 mmol) and 1.5 eqmol of DMAP (1.8 g, 15.0 mmol). The mixture is stirred at room temperature and the reaction is monitored by TLC (alumina, petroleum ether/ethyl acetate 8:2, Rfp=0.50; Rfa=0.76). After 30 minutes dicyclohexylurea is filtered off and the solvent is evaporated off to obtain a crude, which is subsequently purified by column chromatography (35 g of alumina gel, 95:5 petroleum ether-ethyl acetate, fractions: about 20 ml). 4.6 g of product are obtained (84%).

$^1$H NMR (300 MHz, CDCl$_3$): δ 7.25 (m, 5H), 5.41 (m, 1H), 5.29 (m, 1H), 4.86 (quint, J=6.0 Hz, 1H), 4.73 (s, 21-f), 3.58 (s, 2H), 2.45 (br t, J=6.0 Hz, 2H), 2.26 (m, 2M), 1.96 (m, 2H), 1.68 (m, 2H), 1.51 (m, 2H), about 1.29 (br m), about 1.21 (br m), 0.86 (br t, J=7.1 Hz, 3H).

EXAMPLE V

12-Phenylacetyl Ricinoleic Acid 4.6 g (8.4 mmol) of 2',2',2'-trichloroethyl 12-phenylacetyl ricinoleate are dissolved in 40 ml of a 1:1 acetic acid/McOH solution, then added with 4.6 g of activated zinc powder under strong stirring, and the reaction is monitored by TLC (petroleum ether/ethyl acetate 8:2; Rfp=0.69; Rfa=0.36). After 18 hrs the mixture is filtered through Celite, washing with ethyl acetate. The filtrate is concentrated, washed with water and with a sodium bicarbonate saturated solution, then dried over sodium sulphate, filtered and evaporated. The crude is purified by column chromatography (60 g of silica gel, 95:5 petroleum ether-ethyl acetate, fractions: about 20 ml). 1.85 mg of product (53%) are obtained.

$^1$H NMR (300 MHz): δ 7.25 (m, 5H), 5.41 (m, 1H), 5.26 (m, 1H), 4.86 (quint, J=6.0 Hz, 1H), 3.58 (s, 2H), 2.34 (t, J=6.0 Hz, 2H), 2.28 (br t, J=6.7 Hz, 2H), 1.97 (m, 2H), 1.62 (m, 2H), 1.51 (m, 21-f), about 1.29 (br m), about 1.21 (br m), 0.86 (br t, J=7.1 Hz, 3H).

EXAMPLE VI

12-Phenylacetyl Rinvanil 1.85 g of 12-phenylacetyl ricinoleic acid are dissolved (4.4 mmol) in 15 ml of dry dichloromethane and added with 2 eqmol of vanillamine hydrochloride (835 mg, 4.4 mmol), 4 eqmol of TEA (2.45 ml, 1.78 g, 17.6 mmol) and 1.2 eqmol of polyphosphoric acid (50% EtOH solution, 3.4 ml, 1.68 g, 5.28 mmol). The reaction is left under stirring at room temperature and monitored by TLC (6:4: Rfp=0.67; Rfa=0.37). After 3 hrs the solvent is evaporated off and the crude is purified by column chromatography (50 g of silica gel, eluted with 7:3 petroleum ether/ethyl acetate, fractions: about 20 ml). The product is further purified by filtration through alumina (6:4 to 4:6 petroleum ether/ethyl acetate). 512 mg of phenylacetyl rinvanil are obtained (23%).

EXAMPLE VII

2',2',2'-Trichloroethyl 12-Benzoyl Ricinoleate 200 mg of 2',2',2'-trichloroethyl ricinoleate (M.W.=429.85; 0.46 mmol) are dissolved in 2 ml of toluene and added with 1 eqmol of benzoic acid (M.W.=122.12; 0.46 mmol, 56 mg), 1 eqmol of dicyclohexylcarbodiimide (M.W.=206.33; 0.46 mmol, 95 mg) and 1 eqmol of DMAP (M.W.=122.17; 0.46 mmol, 56 mg). The mixture is stirred at room temperature and the reaction is monitored by TLC (95:5 hexane/ethyl acetate, Rfp=0.05; Rfa=0.32). After 30 minutes one more equivalent of benzoic acid, dicyclohexylcarbodiimide and DMAP is added. Even if the reaction is not complete, it is worked up after further 18 hours stirring: dicyclohexylurea is filtered and the filtrate is evaporated. The crude is purified by column chromatography (5 g of silica gel, 95:5 hexane/ethyl acetate, fractions of about 5 ml were collected). 195 mg of product are obtained (79%).

$^1$H NMR (300 MHz): δ 8.03 (Bz AA'), 7.61 (Bz C), 7.52 (Bz BB'), 5.42 (m, 2H), 5.14 (quint, J=6.0 Hz, 1H), 4.73 (s, 2H), 3.60 (br t, J=6.0 Hz, 2H), 2.43 (m, 4H), 2.02 (m, 2H), about 1.64 (m, 2H), about 1.20 (br m, 20H), 0.86 (br t, J=7.1 Hz, 3H).

$^{13}$C-NMR (75 MHz, CDCl$_3$): 177.0 (s), 173.5 (s), 171.7 (s), 156.6 (s), 147.2 (s), 145.4 (s), 141.6 (d), 136.8 (s), 132.7 (S), 130.2 (d), 129.5 (d), 129.3 (d), 128.5 (d), 128.3 (d), 127.5 (d), 127.0 (d), 126.2 (d), 124.1 (d), 120.6 (d), 114.9 (d), 110.9 (d), 106.1 (d), 74.6 (d), 56.3 (q), 43.8 (t), 43.4 (t), 41.9 (t), 36.6 (t).4, 31.8 (t), 29.1 (t), 27.2 (t), 25.9 (t), 25.3 (t), 22.6 (t), 13.9 (q).

CI-MS: 552 (M+H)$^+$.

EXAMPLE VIII

12-Benzoyl Ricinoleic Acid 185 mg of 2',2',2'-trichloroethyl 12-benzoylricinoleate (M.W.=533.95; 0.35 mmol) are dissolved in 2 ml of a 1:1 acetic acid/MeOH solution, then added with 200 mg of activated zinc powder under strong stirring and the reaction is monitored by TLC (8:2 hexane/ethyl acetate; Rfp=0.42; Rfa=0.17). After 3 hrs the mixture is filtered through celite washing with ethyl acetate. The organic phase is concentrated, washed with water and a sodium bicarbonate solution, then dried over sodium sulfate, filtered and evaporated. The residue is purified by column chromatography (2.5 g of silica gel, 95:5 petroleum ether/ethyl acetate, fractions of about 5 ml are collected). 68 mg of product (48%) are obtained.

$^1$H NMR (300 MHz, CDCl$_3$): δ 8.02 (Bz AA'), 7.54 (Bz C), 7.43 (Bz BB'), 5.43 (m, 2H), 5.12 (quint, J=6.0 Hz, 1H), 3.60 (br t, J=6.0 Hz, 2H), 2.42 (t, J=7.4 Hz, 21-4), 2.34 (t, J=7.4 Hz), 2.01 (m, 2H), about 1.64 (m, 4H), about 1.26 (br m, 20H), 0.86 (br t, J=7.1 Hz, 3H).

EXAMPLE IX

12-Benzoyl Rinvanil 60 mg of 12-benzoyl ricinoleic acid (M.W.=402.57; 0.15 mmol) are dissolved in 2 ml of dry dichloromethane and added with 2 eqmol of vanillamine hydrochloride (M.W.=189.64; 0.30 mmol; 56.89 mg), 8 eqmol of TEA (M.W.=101; 1.2 mmol; 121 mg; d=0.726; 167 µl) and 3 eqmol of polyphosphoric acid (M.W.=318.19; 0.45 mmol; 34.2 mg; 50% EtOH solution, 68 µl). The mixture is left under stirring at room temperature and the reaction is monitored by TLC (8:2 petroleum ether/ethyl acetate; Rfp=0.41; Rfa=0). After 2 hours the reaction solvent is evaporated off and the crude is purified by column chromatography (2.5 g of silica gel, 8:2 petroleum ether/ethyl acetate, fractions: about 5 ml). 31 mg of benzoyl rinvanil (38%) are obtained.

$^1$H NMR (300 MHz, CDCl$_3$): δ 8.02 (Bz AA'), 7.54 (Bz C), 7.42 (Bz BB'), 6.84 (dd, J=8, 3 Hz, 1H), 6.79 (d, J=3 Hz, 1H), 6.74 (d, J=8 Hz, 1H), 5.78 (br s, 1H), 5.41 (m, 2H), 5.11 (quint, J=6.0 Hz, 1H), 4.33 (d, J=5.8 Hz, 2-H), 3.85 (s, 3H), 3.60 (br t, J=6.0 Hz, 2H), 2.40 (m, 2H), 2.16 (t, J=7.4 Hz), 2.01 (m, 2H), about 1.64 (m, 4H), about 1.26 (br m, 20H), 0.85 (br t, J=7.1 Hz, 3H).

EXAMPLE X

9,10-Methyl Rinvanil

In a two-neck round-bottom flask and under nitrogen atmosphere, 300 mg of rinvanil (M.W.=433.62; 0.69 mmol) are dissolved in 29 ml of anhydrous toluene (29 ml) and treated with 15 eqmol of diethylzine (1.0 M in hexane; 10.35 mmol; 10.35 ml) and 15 eqmol of bis-iodomethane (M.W.=268.84; 10.35 mmol; 2.78 g; d=3.325 g/ml; 837 µl). The solution is stirred at 65° C. and turns pink when a white solid starts to precipitate. The reaction is monitored by TLC on silver silica (6:4 petroleum ether/ethyl acetate; Rfp=0; Rfa=0.1).

After 7 hours the mixture is cooled to 0° C., added with 2N H$_2$SO$_4$ and extracted with ethyl acetate, then the organic phase is washed with NaHCO$_3$ and brine. After drying (Na$_2$SO$_4$) and evaporation, the crude is purified by column chromatography (15 ml of silica, packed with petrol ether/ethyl acetate 7:3 and eluted with a 6:4 mixture of the same solvents; fractions: about 8 ml). 119 mg of product (40%) are obtained.

$^1$H NMR (300 MHz, CDCl$_3$): δ 6.85 (d, J=7.9 Hz, 1H), 6.80 (d, J=2.0 Hz, 1H), 6.74 (dd, J=7.9, 2.0 Hz, 1H), 5.70 (br s, 1H), 5.65 (br s, 1H), 4.36 (d, J=5.8 Hz, 2H), 3.88 (s, 3H), 3.76 (quint, J=6.0 Hz, 1H), 2.17 (t, J=7.4 Hz), 1.27 (br m), 1.20 (br m), 0.835 (br t, J=7.1 Hz, 3H), 0.61 (m, 2H).

CI-MS: 448 (M+H)$^+$.

EXAMPLE XI

9,10-Methylen-12,4'-Diphenyl Acetyl Rinvanil 100 mg of 9,10-methyl rinvanil (M.W.=447.65; 0.22 mmol) are dissolved in 2 ml of toluene and added with 2 eqmol of phenylacetic acid (M.W.=136; 0.44 mmol; 60 mg), 2 eqmol of dicyclohexylcarbodiimide (M.W.=202; 0.44 mmol; 89 mg) and 1 eqmol of DMAP (M.W.=122; 0.22 mmol; 27 mg). The mixture is left under stirring at room temperature and the reaction is monitored by TLC (6:4 petroleum ether/ethyl acetate Rfp=0.23; Rfa=0.42). After 3 hours dicyclohexylurea is removed by filtration and the solvent is evaporated off. The resulting crude can be used as such for the subsequent reaction or purified by chromatography (5 g of silica gel, 8:2 petroleum ether/ethyl acetate as the eluent).

$^1$H NMR (300 MHz, CDCl$_3$): δ 7.39-7.17 (m, 10H), 6.93 (d, J=7.9 Hz, 1H), 6.85 (d, J=2.0 Hz, 1H), 6.80 (dd, J=7.9, 2.0 Hz, 1H), 5.72 (br s, 1H), 5.64 (br s, 1H), 4.93 (quint, J=6.0 Hz, 1H), 4.34 (d, J=5.8 Hz, 2H), 3.87 (s, 3H), 3.65 (d, J=15 Hz, 1H), 3.59 (d, J=15 Hz, 1H), 2.17 (t, J=7.4 Hz), 1.27 (br m), 1.20 (br m), 0.84 (br t, J=7.1 Hz, 3H), 0.57 (m, 2H).

$^{13}$C-NMR (75 MHz, CDCl$_3$): 175.5 (s), 173.9 (s), 149.7 (s), 147.1 (s), 134.5 (s), 132.2 (d), 130.4 (s), 128.2 (d), 128.1 (d), 127.5 (d), 124.2 (d), 120.8 (d), 114.6 (d), 110.3 (d), 75.6 (d), 56.0 (q), 43.6 (t), 41.9 (t), 33.2 (t).4, 31.8 (t), 30.1 (t), 29.5 (t), 39.4 (t), 25.9 (t), 25.1 (t), 22.6 (t), 14.2 (q), 11.0 (t).

CI-MS: 684 (M+H)$^+$.

EXAMPLE XII

9,10-Methylen-12-Phenylacetyl Rinvanil I

The crude 9,10-methylen-12,4'-diphenylacetyl rinvanil from example XI (0.22 mmol, teorethical) is dissolved in dichloromethane (20 ml) and added with 5 eqmol of pyrrolidine (M.W.=71.12; 1.1 mmol; 78 mg; d=0.86 g/ml; 90 μL). After 3 hours the reaction is complete (TLC over alumina, eluent: 6:4 petrol ether/ethyl acetate; Rfp=0.8; Rfa=0.5; Rfb=0.45; TLC on silica with the same eluent: Rfp=0.42; Rfa=0.39; one spot only is evidenced). The organic phase is washed with 2N H$_2$SO$_4$ and brine and dried over sodium sulfate. After evaporation of the solvent, the crude is purified by column chromatography (10 ml of silica, 7:3 to 4:6 petroleum ether/ethyl acetate). 75 mg of product (60%) are obtained.

$^1$H NMR (300 MHz): δ 7.26 (m, 5H), 6.86 (d, J=7.9 Hz, 1H), 6.80 (d, J=2.0 Hz, 1H), 6.74 (dd, J=7.9, 2.0 Hz, 1H), 5.70 (br s, 1H), 5.65 (br s, 1H), 4.95 (quint, J=6.0 Hz, 1H), 4.33 (d, J=5.8 Hz, 2H), 3.86 (s, 3H), 3.60 (s, 2H), 2.17 (t, J=7.4 Hz), 1.63-1.52 (m, 6H), 1.27 (br m), 0.84 (br t, J=7.1 Hz, 3H), 0.58 (m, 3H), −0.30 (m, 1H).

EXAMPLE XIII

TPRV1 Binding Assay

Affinity for human TRPV1 was measured by displacement of [3H]RTX (48 Ci/mmol, NEN-Dupont) from HEK cells membranes (50 μg/tube) according to the method described by Ross (Ross et al., Br. J. Pharmacol. 2001, 132, 631-640). In these conditions Kd and Bmax for [$^3$H]RTX were 0.5 nM and 1.39 pmol/mg protein. The Ki of the displacement of 1 nM [3]RTX was calculated from the IC$_{50}$ value (obtained with GraphPad Software) using Cheng-Prusoff's equation. Specific binding was calculated with 1 μM RTX (Alexis Biochemicals) and was 48.1+5.6%. The values for the compounds of the invention are reported in Table 1.

EXAMPLE XIV

4'-(2-Aminoethyl)-12-Phenylacetyl Rinvanil (Hydrochloride)

In a two-neck round-bottom flask and under nitrogen atmosphere, a solution of 382 mg of phenylacetyl rinvanil (M.W.=552; 0.69 mmol) dissolved in THF (5 ml) is added to a suspension of NaH (60%, 57 mg, 1.4 mmol, 2 molar equivalents) in THF (10 ml). After stirring at room temperature for 10 min, an excess of 1,2-dibromoethane (0.7 ml) is added. The solution is stirred at room temperature for 16 hours, then diluted with saturated NH$_4$Cl and extracted with ether. Evaporation of the solvent affords an oil, which is filtered through a thin silica bed (15 g) using petroleum ether (100 ml) to remove the excess of 1,2-dibromoethane, then 1:1 petroleum ether/ethyl acetate (100 ml) to elute the product. After evaporation of the solvent, a gluey residue is obtained, which is directly dissolved in dimethylformamide (10 ml) and treated with an excess of sodium azide (NaN$_3$) (300 mg). After stirring at room temperature for 16 hours, the reaction is diluted with water (about 50 ml) and extracted with 3:1 petroleum ether/ether (2×30 ml). After washing with saturated NaCl and drying (Na$_2$SO$_4$), the organic phase is evaporated, and the residue is dissolved in THF (20 ml), then added with triphenylphosphine (917 mg, 3.5 mmol) and water (0.62 ml, 3.5 mmol). After stirring for 5 hours at room temperature, the reaction is diluted with water and extracted with ethyl acetate. After drying (Na$_2$SO$_4$) and evaporation, the residue is purified by chromatography on a silica gel column (10 g), using ethyl acetate as the eluent. 130 mg of product are obtained (overall yield: 40%).

$^1$H NMR (300 MHz, CDCl$_3$): δ 7.29 (m, 5H), 6.87 (d, J=7.9 Hz, 1H), 6.81 (d, J=2.0 Hz, 1H), 6.77 (dd, J=7.9, 2.0 Hz, 1H), 5.61 (br s, 1H), 5.42 (m, 1H), 5.29 (m, 1H), 4.83 (quint, J=6.0 Hz, 1H), 4.31 (d, J=5.8 Hz, 2H), 4.01 (d, J=7.0 Hz, 2H), 3.92 (s, 3H), 3.59 (s, 2H), 3.02 (br t, J=7.0 Hz, 2H), 2.21 (m, 2H), 2.19 (t, J=7.4 Hz), 1.96 (m, 2H), 1.65 (m, 2H), 1.52 (m, 2H), 1.29 (br m), 1.24 (br m), 0.84 (br t, J=7.1 Hz, 3H).

$^{13}$C-NMR (75 MHz, CDCl$_3$): 177.1 (s), 173.7 (s), 171.1 (s), 158.9 (s), 147.3 (s), 145.1 (s), 143.6 (d), 138.3 (s), 132.7 (s), 130.8 (d), 129.0 (d), 129.8 (d), 128.5 (d), 128.8 (d), 128.0 (d), 127.2 (d), 126.5 (d), 123.9 (d), 121.1 (d), 115.0 (d), 112.2 (d), 109.2 (d), 74.9 (d), 71.4 (t), 56.1 (q), 47.9 (t), 43.9 (t), 43.1 (t), 42.1 (t), 36.6 (t).4, 31.0 (t), 29.2 (t), 27.2 (t), 26.1 (t), 25.2 (t), 22.6 (t), 13.2 (q).

CI-MS: 596 (M+H)$^+$.

The hydrochloride salt is obtained by dissolving the product in the minimum amount of THF and adding 1 equivalent of a 1.0 M hydrochloric acid solution in diethyl ether at 0° C. After evaporation of the solvent the precipitate is collected and dried under vacuum.

EXAMPLE XV

9,10-Epoxy-12-Phenylacetyl Rinvanil

A solution of 12,4'-diphenylacetyl rinvanil prepared as in example 1 (300 mg, 0.45 mmol) in anhydrous CH$_2$Cl$_2$ (6 ml) is added with 2.5 molar equivalents of meta-chloroperbenzoic acid (MCPBA, 242 mg of 80% acid, 1.12 mmoles), and the solution is magnetically stirred for 3 hours, then washed with Na$_2$S$_2$O$_3$, dried (Na$_2$SO$_4$), filtered and evaporated. The residue is directly dissolved in CH$_2$Cl$_2$ (5 ml) and added with pyrrolidine (155 mg, 0.180 ml, 5 molar equiv.). After stirring at room temperature for 16 hours, the mixture is washed with 2N H$_2$SO$_4$ and saturated NaCl, then dried (Na$_2$SO$_4$). After evaporation of the solvent the residue is purified by column chromatography on neutral alumina (3 g, 6:4 petroleum ether/ethyl acetate as eluent), to obtain 120 mg of product (41%).

$^1$H NMR (300 MHz, CDCl$_3$): δ 7.26 (m, 5H), 6.87 (d, J=7.9 Hz, 1H), 6.82 (br s, 1H), 6.78 (br d, J=7.9 Hz, 1H), 5.69 (br s, 1H), 5.64 (br s, 1H), 5.05 (quint, J=6.0 Hz, 1H), 4.37 (d, J=5.8 Hz, 2H), 3.89 (s, 3H), 3.66 (m, 2H), 2.90 (m, 1H), 2.84 (m, 1H), 2.20 (t, J=7.4 Hz, 2H), about 1.76 (m), 1.44 (m), 1.27 (br m), 1.20 (br m), 0.88 (br t, J=7.1 Hz, 3H).

$^{13}$C-NMR (75 MHz, CDCl$_3$): 173.0 (s), 171.4 (s), 146.8 (s), 145.2 (s), 134.2 (s), 130.4 (s), 129.3 (d), 128.6 (d), 128.3 (d), 127.3 (d), 127.2 (d), 120.9 (d), 114.5 (d), 110.8 (d), 73.0 (d), 57.0, 56.4 (d), 56.0 (t), 53.6, 53.0 (d), 43.6 (t), 41.8 (t), 36.8 (t).4, 31.7 (t), 29.4 (t), 29.2 (t), 27.5 (t), 25.8 (t), 25.3 (t), 22.6 (t), 14.2 (q).

CI-MS: 568 (M+H)$^+$.

EXAMPLE XVI

4'-(2-Aminoethyl)-12-Phenylacetyl Rinvanil.HCl Injectable Solution

4'-(2-Aminoethyl)-12-phenylacetyl rinvanil.HCl injectable solution consists of 4'-(2-aminoethyl)-12-phenylacetyl rinvanil.HCl (1.0 mg), sodium chloride (9.0 mg), benzyl alcohol (15.0 mg) and water for injectable preparations (up to 1 ml).

In the standard procedure sodium chloride and benzyl alcohol are dissolved in water for injectable preparations, then 4'-(2-aminoethyl)-12-phenylacetyl rinvanil hydrochloride is added.

EXAMPLE XVII

12-Phenylacetyl Rinvanil Injectable Solution

12-Phenylacetyl rinvanil injectable solution consists of 12-phenylacetyl rinvanil (1.0 mg), propyl gallate (0.5 mg), olive oil for injectable preparations (up to 1 ml).

EXAMPLE XVIII

Emulsion for Topical Use

Emulsions for topical use, for example 12-phenylacetyl rinvanil emulsions, consist of 12-phenylacetyl rinvanil (1.0 g), liquid paraffin (25.0 g), stearyl alcohol (12.0 g), cetyl alcohol (5.0 g), methyl p-hydroxybenzoate (0.028 g), propyl p-hydroxybenzoate (0.012 g), PEG-40 stearate (1.0 g), glycerin (12.0 g), purified water (up to 100 g).

In the standard procedure liquid paraffin, stearyl alcohol and cetyl alcohol are melted at 70-75° C. under stirring, then 12-phenylacetyl rinvanil is dissolved in the resulting phase, keeping the solution at 70-75° C. The remaining components, previously dissolved in purified water at 70-75° C., are then added under strong stirring at 70-75° C. The resulting product is slowly cooled under stirring.

The invention claimed is:

1. A compound of the general formula (I)

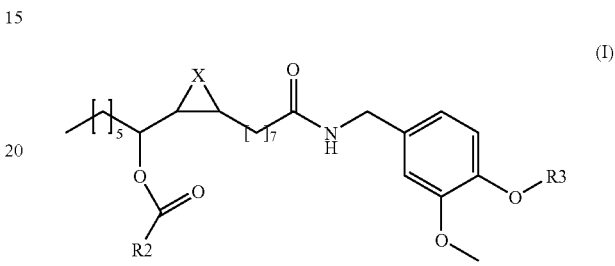

in which
X represents two hydrogen atoms, a π-bond, oxygen or methylene;
R2 is a $C_6$-$C_{12}$ aryl or arylalkyl residue;
R3 is hydrogen, 2-hydroxyethyl or 2-aminoethyl.

2. The compound as claimed in claim 1 wherein R2 is phenyl, benzyl or phenethyl.

3. The compound as claimed in claim 1 wherein R3 is hydrogen.

4. A method for the treatment of urinary incontinence, for the relief of neuropathic pain and for the therapy of intestinal inflammatory disorders, comprising administering to a subject in need thereof an effective amount of a compound according to claim 1.

5. A composition containing one or more of the compounds of claim 1, in admixture with suitable carriers.

6. The compound as claimed in claim 2 wherein R3 is hydrogen.

* * * * *

UNITED STATES PATENT AND TRADEMARK OFFICE
CERTIFICATE OF CORRECTION

PATENT NO.        : 7,429,673 B2
APPLICATION NO.   : 11/658737
DATED             : September 30, 2008
INVENTOR(S)       : Paolo Morazzoni et al.

It is certified that error appears in the above-identified patent and that said Letters Patent is hereby corrected as shown below:

On the title page, please amend item (57) to read as follows:

-- ABSTRACT

The compounds of the general formula (I) in which X represents two hydrogen atoms, a π-bond, oxygen or methylene; R2 is a $C_6$-$C_{12}$ aryl, or arylalkyl residue; R3 is hydrogen, 2-hydroxyethyl or 2-aminoethyl are useful for the treatment of pathologies mediated by vanilloid receptors type I.

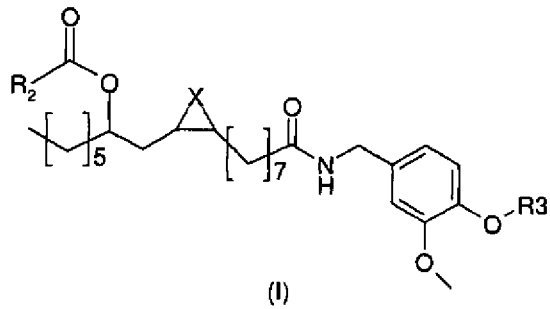

In column 2, lines 2-11, please delete general formula (I) and insert:

--

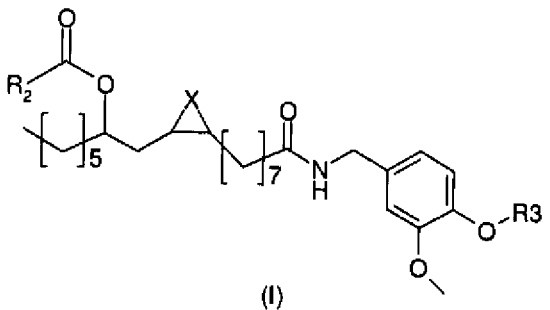

--

UNITED STATES PATENT AND TRADEMARK OFFICE
CERTIFICATE OF CORRECTION

PATENT NO. : 7,429,673 B2  Page 2 of 4
APPLICATION NO. : 11/658737
DATED : September 30, 2008
INVENTOR(S) : Paolo Morazzoni et al.

It is certified that error appears in the above-identified patent and that said Letters Patent is hereby corrected as shown below:

In column 2, line 42 to column 3, line 20, please delete Scheme 1 and insert:

-- Scheme 1

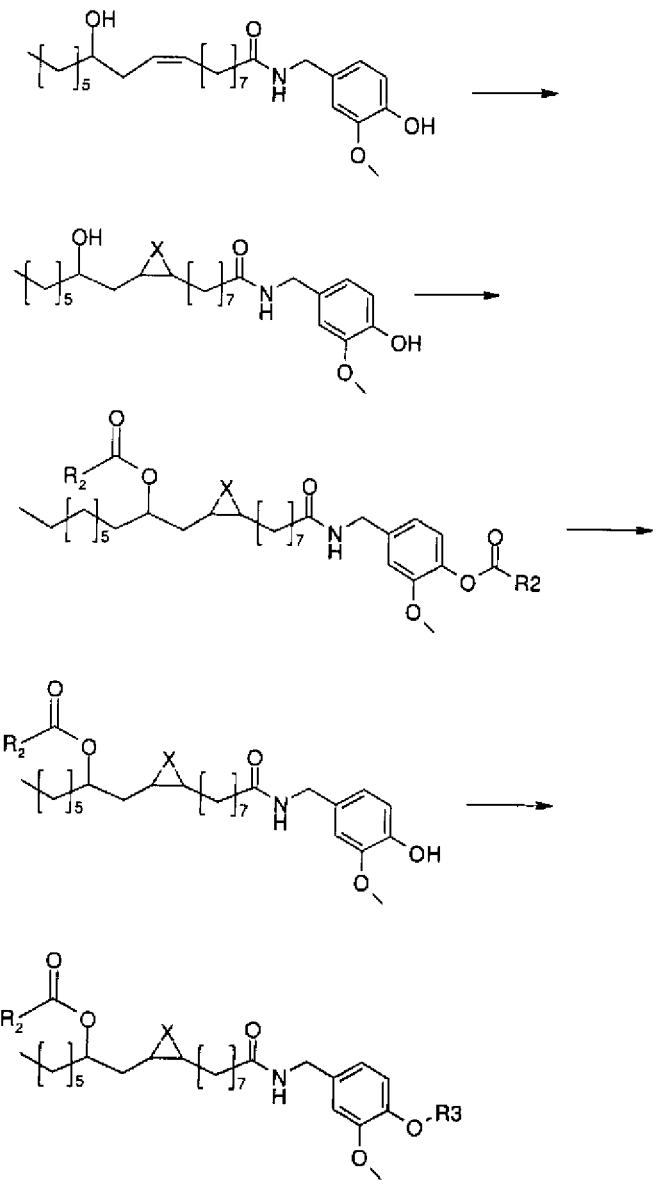

--

UNITED STATES PATENT AND TRADEMARK OFFICE
CERTIFICATE OF CORRECTION

PATENT NO.       : 7,429,673 B2
APPLICATION NO.  : 11/658737
DATED            : September 30, 2008
INVENTOR(S)      : Paolo Morazzoni et al.

It is certified that error appears in the above-identified patent and that said Letters Patent is hereby corrected as shown below:

In column 2, line 42 to column 3, lines 40-49 and column 4, lines 1-30, please delete Scheme 2 and insert:

-- Scheme 2

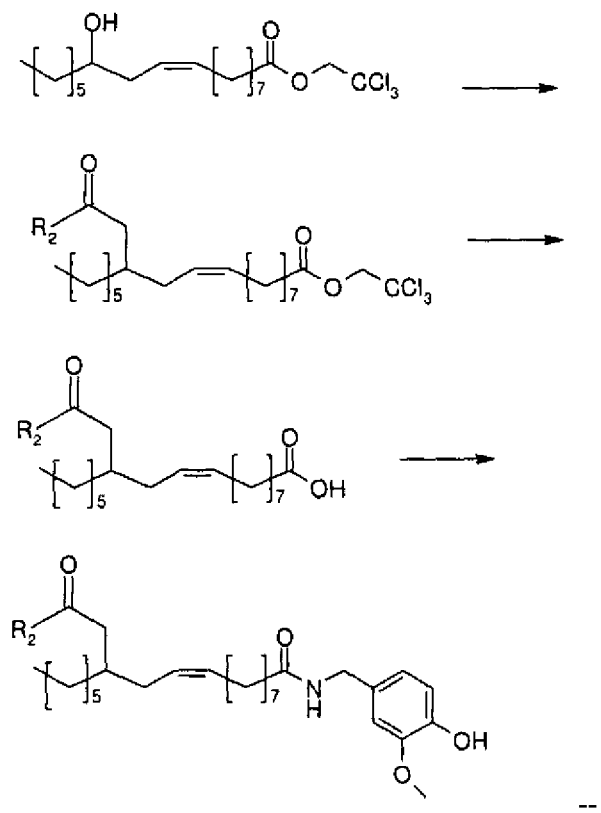

--

UNITED STATES PATENT AND TRADEMARK OFFICE
CERTIFICATE OF CORRECTION

PATENT NO. : 7,429,673 B2
APPLICATION NO. : 11/658737
DATED : September 30, 2008
INVENTOR(S) : Paolo Morazzoni et al.

It is certified that error appears in the above-identified patent and that said Letters Patent is hereby corrected as shown below:

In claim 1 at column 14, lines 15-25 please delete formula (I) and insert:

--

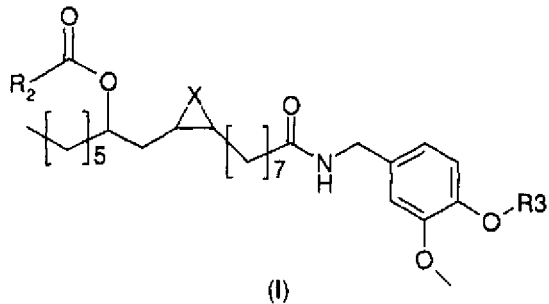

(I)

--

Signed and Sealed this

Twenty-fifth Day of August, 2009

David J. Kappos
*Director of the United States Patent and Trademark Office*